United States Patent
Zeun et al.

(10) Patent No.: US 9,383,317 B2
(45) Date of Patent: Jul. 5, 2016

(54) OPTICAL SENSOR, ESPECIALLY FOR DETERMINING SUBSTANCE CONCENTRATIONS IN AQUEOUS SOLUTIONS BY MEANS OF A FLUORESCENCE MEASUREMENT

(75) Inventors: Hendrik Zeun, Chemnitz (DE); Ronny Michael, Erlau (DE)

(73) Assignee: Endress+Hauser Conducta GmbH+Co. KG (DE)

( * ) Notice: Subject to any disclaimer, the term of this patent is extended or adjusted under 35 U.S.C. 154(b) by 810 days.

(21) Appl. No.: 13/590,420

(22) Filed: Aug. 21, 2012

(65) Prior Publication Data

US 2013/0214175 A1 Aug. 22, 2013

(30) Foreign Application Priority Data

Aug. 22, 2011 (DE) .......................... 10 2011 081 326

(51) Int. Cl.
*G01N 21/64* (2006.01)
*G01N 21/84* (2006.01)
*G01D 5/34* (2006.01)

(52) U.S. Cl.
CPC ............ *G01N 21/64* (2013.01); *G01N 21/6428* (2013.01); *G01N 21/8422* (2013.01); *G01D 5/34* (2013.01)

(58) Field of Classification Search
CPC G01N 21/643; G01N 21/645; G01N 21/8507
See application file for complete search history.

(56) References Cited

U.S. PATENT DOCUMENTS

| | | | |
|---|---|---|---|
| 4,200,100 A | 4/1980 | Willis | |
| 4,716,118 A | 12/1987 | Wolfbeis | |
| 4,907,037 A | 3/1990 | Boisde | |
| 4,925,268 A * | 5/1990 | Iyer et al. | ......................... 385/12 |
| 5,652,810 A * | 7/1997 | Tipton et al. | ..................... 385/12 |
| 6,730,471 B1 | 5/2004 | Katerkamp | |
| 7,838,835 B2 * | 11/2010 | Thomson | .................. 250/339.07 |
| 2004/0086215 A1* | 5/2004 | Salerno et al. | ................... 385/12 |
| 2008/0013103 A1* | 1/2008 | Inoue | ..................... G01B 11/25 356/610 |

FOREIGN PATENT DOCUMENTS

| | | |
|---|---|---|
| DE | 2654726 B1 | 3/1978 |
| DE | 3430935 A1 | 3/1985 |
| DE | 3889757 T2 | 12/1994 |
| DE | 19524207 A1 | 6/1996 |

(Continued)

OTHER PUBLICATIONS

German Search Report, Nov. 9, 2011, German Patent Office, Munich, Germany.

*Primary Examiner* — Jill Warden
*Assistant Examiner* — Matthew Krcha
(74) *Attorney, Agent, or Firm* — Christopher R. Powers; PatServe

(57) ABSTRACT

An optical sensor, comprising a sensor head, which contains a sensitive element and which is adjoined by a housing, which contains sensor electronics, wherein the sensitive element is irradiated with light from an optical transmitter and a light characteristic radiated back by the sensitive element is detected by an optical receiver and evaluated by the sensor electronics. The sensor head and the housing are embodied to be separable, wherein different sensor heads having different sensitive elements are connectable to the housing containing the sensor electronics and the sensor electronics evaluates the light characteristics generated by the different sensitive elements.

12 Claims, 1 Drawing Sheet

(56) References Cited

FOREIGN PATENT DOCUMENTS

| | | |
|---|---|---|
| DE | 19903506 A1 | 8/2000 |
| DE | 102005033926 B4 | 1/2007 |
| EP | 0126600 A2 | 11/1984 |
| EP | 0372802 A2 | 6/1990 |
| EP | 0597566 A1 | 5/1994 |
| EP | 2295953 A1 * | 3/2011 |
| GB | 1589333 | 5/1981 |
| WO | WO 91/03730 | 3/1991 |
| WO | WO 02/088686 A1 | 11/2002 |
| WO | WO 2007014539 A1 * | 2/2007 |

* cited by examiner

OPTICAL SENSOR, ESPECIALLY FOR DETERMINING SUBSTANCE CONCENTRATIONS IN AQUEOUS SOLUTIONS BY MEANS OF A FLUORESCENCE MEASUREMENT

TECHNICAL FIELD

The invention relates to an optical sensor, especially for determining substance concentrations in aqueous solutions by means of a fluorescence measurement, comprising a sensor head, which contains a sensitive element and which is adjoined by a housing, which contains a sensor electronics, wherein the sensitive element is irradiated with light from an optical transmitter and a light characteristic radiated back by the sensitive element is detected by an optical receiver and evaluated by the sensor electronics.

BACKGROUND DISCUSSION

A system for measuring substance concentrations in solutions on the basis of a fluorescence measurement is known from EP 2 295 953 A1, in which an optical sensor is releasably connected to a structurally compact measuring unit. The optical sensor includes a sensor head, which is inseparably connected to a housing, which contains a signal evaluation electronics. The housing, moreover, has a light source, which radiates an excitation radiation into a liquid to be examined. With this excitation radiation, a sensitive element, which is arranged in the medium to be examined and is contained in the sensor head, is excited. This sensitive element radiates light back as a function of the substance concentration.

The fluorescent radiation radiated back by the sensitive element is received by a detector unit and forwarded to the sensor electronics. Depending on the properties of the sensitive element, the optical sensor reacts to different particle concentrations with different light intensities, frequencies or decay curves.

A cap for use with optical sensors is known from WO 2007/014539 A1, wherein the cap is embodied replaceably for a connection piece, which contains optical or optoelectronic components. The sensitive element, which is used for the measurement of physical or chemical parameters, is arranged in the cap in such case. In order to assure that the right sensitive element is always secured to the connection piece that fits thereto, the cap and the connection piece are protected against mix-ups by complementary coding options.

It is disadvantageous in these arrangements that an individual sensor for each measurement parameter must be developed and manufactured, which leads to a high production effort.

SUMMARY OF THE INVENTION

An object of the invention, thus, is to provide an optical sensor, whose manufacture is simplified.

According to the invention, the object is achieved by features including that the sensor head and the housing are embodied to be separable, wherein different sensor heads having different sensitive elements are connectable to the housing containing the sensor electronics and the sensor electronics evaluates the light characteristics generated by the different sensitive elements. This has the advantage that a single sensor electronics can be utilized for different measurement parameters ascertained by different sensitive elements. In this way, the manufacture of the optical sensor is simplified, since the sensor electronics is designed for all sensor heads, although the sensor heads contain different sensitive elements. Thus, the concentration of ions or molecules, for example, oxygen, chlorine, hydrogen, carbon monoxide, carbon dioxide, nitrate, ammonium, phosphate, sodium, potassium, chemical compounds containing chloride or chlorine, or the pH value can be measured using the same sensor electronics without requiring changes to the sensor electronics. The sensor electronics must only be properly equipped in regards to the software, in order to be able to exactly evaluate the light characteristics, which are emitted by the respective sensitive layer. The housing having the sensor electronics, can thus be manufactured in large quantities and can be first connected to the sensor head containing the desired sensitive element at the end of the manufacturing process.

Advantageously, the sensor head and the housing are optically and mechanically connected to one another via a standard interface. Such a standard interface offers the advantage that a simple securement or replacement of the sensor head is possible. Thus, a user of the optical sensor can, at any time, apply to the housing the sensor head, with which a desired measurement parameter can be measured. It is, indeed, necessary, that different sensor heads, which are equipped with the different sensitive elements, be present; then, when required, these can simply be applied to the housing having the sensor electronics. There is no requirement to keep a number of the most varied of optical sensors on hand. Due to the application of the standard interface a simple replacement of the sensor head is possible.

In an embodiment the sensor head is cap-like. The cap-like embodiment enables a sufficient protection of the sensitive element contained in the stable cap from outer influences.

Moreover, the cap can also be simply held manually without the occurrence of a mechanical influencing of the sensitive element in the sensor head.

In a variant, the cap-like embodiment of the sensor head or the housing has a sealing element, which seals off the standard interface from the environment. In this way, it is assured that no measured medium can penetrate into the optical sensor and contaminate the sensitive element.

In a further development, the sensitive element is embodied as a sensitive layer. This embodiment enables a constructively small sensor head.

In a variant, the housing contains the optical transmitter and the optical receiver, which are connected to the sensor electronics, wherein the sensor electronics has a memory containing measurement data and/or characteristic lines of the light characteristics of the different sensitive elements. Thus, new measurement parameters can be made known to the sensor electronics at any time, in that their light characteristics are stored in the memory. If the sensor electronics was previously equipped only for detecting oxygen, or hydrogen, then, for example, at any time, the corresponding light characteristic for the concentration measurement of chlorine can be introduced into the memory, whereby the scope of use of the housing containing the sensor electronics can be enlarged at any time.

Advantageously, the sensor electronics is embodied to recognize the sensitive element in the sensor head automatically. In a calibration or initializing step, the sensor electronics activates the optical transmitter, which radiates light on the sensitive element. The light radiated back is fed to the sensor electronics, which automatically detects the measurement parameter to be determined. Then, in the sensor electronics, an evaluating method is selected, which corresponds to the determined measurement parameter and with which the following concentration measurement methods are executed.

In a form of embodiment, the optical transmitter for radiating light is excitable by the sensor electronics, wherein the light characteristic radiated back by the sensitive element is forwarded from the optical receiver to the sensor electronics, which compares the light characteristic with the stored measurement data and/or characteristic lines for recognizing the sensitive element. Thus, the sensor electronics is not only able to automatically detect the measurement parameter, but can also process a number of measurement parameters. In this embodiment only a single sensor electronics is required for a number of sensors.

In a further development, the stored measurement data comprise light intensities and/or light frequencies and the characteristic lines comprise the decay curves of the light intensity of the light radiated back. On the basis of these specific light characteristics, it is very simple for the sensor electronics to recognize which sensitive element is contained in the cap installed on the housing and which measurement parameter should be evaluated for the optical concentration measurement.

In an embodiment, the sensor electronics has an electrical current source. In this way, it is assured that a sensor so equipped can be applied autarkically at any location.

BRIEF DESCRIPTION OF THE DRAWINGS

The invention allows numerous forms of embodiment. One such embodiment will now be explained in greater details based on the appended drawing, the figures of which show as follows.

DETAIL DISCUSSION IN CONJUCTION WITH THE DRAWINGS

Figure 1:
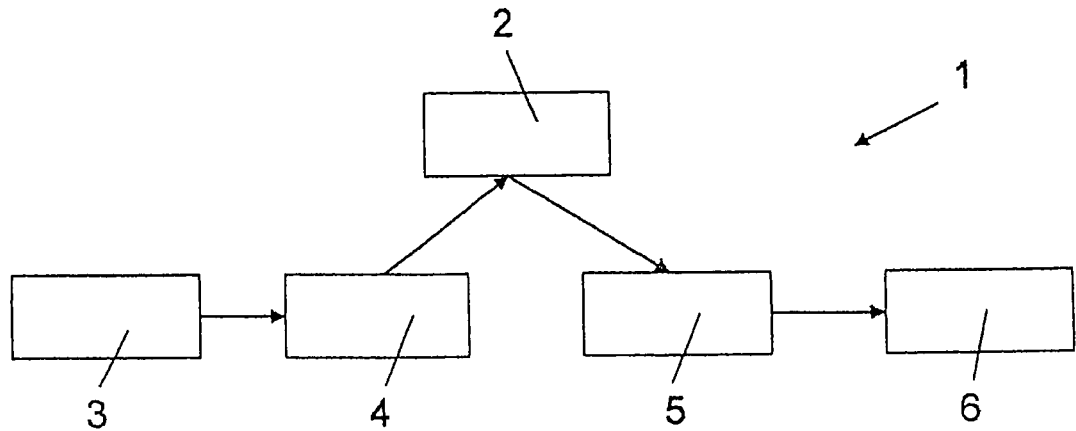
FIG. 1 is a schematic diagram of an optical sensor for optical concentration measurements.

FIG. 1 shows a schematic diagram of an optical sensor 1 for optical concentration measurements, wherein concentration is determined by means of a fluorescence measurement. In such case, a fluorescing layer is arranged as a sensitive element 2 in the optical sensor 1; the fluorescing layer is arranged in a medium (not shown) to be examined. The medium to be investigated can be an aqueous solution, such as, for example, drinking water or industrial water, wherein a material in the medium to be investigated accumulates, e.g. adsorbs, on fluorescing layer 2. Optical sensor 1 includes an electrical current source 3, which supplies energy to an optical transmitter 4, for example, an LED, whereby optical transmitter 4 radiates light on fluorescing layer 2. Fluorescing layer 2 radiates back a light characteristic, which depends on the concentration of the material to be examined on fluorescing layer 2. An optical receiver 5 converts the light characteristic to an electrical signal. The electrical signal produced by optical receiver 5 is fed to an amplifier 6, which amplifies the electrical signal and forwards it to more of the sensor electronics, not shown in further detail. Depending on the properties of fluorescing layer 2, optical sensor 1 reacts to different particle concentrations either with different light intensities, wherein optical sensor 1 absorbs a part of the light radiated by optical transmitter 4, or the wavelengths of the reflected light shift, causing color changes. If a part of the radiated light is absorbed, which results in the change of the light intensity over time, so called decay curves are evaluated, wherein such decay curves especially represent the change of the intensity of the light at a selected wavelength over time. In order to ascertain frequency or color changes, a number of optical receivers 5, which react to specific wavelengths, are necessary.

Figure 2:
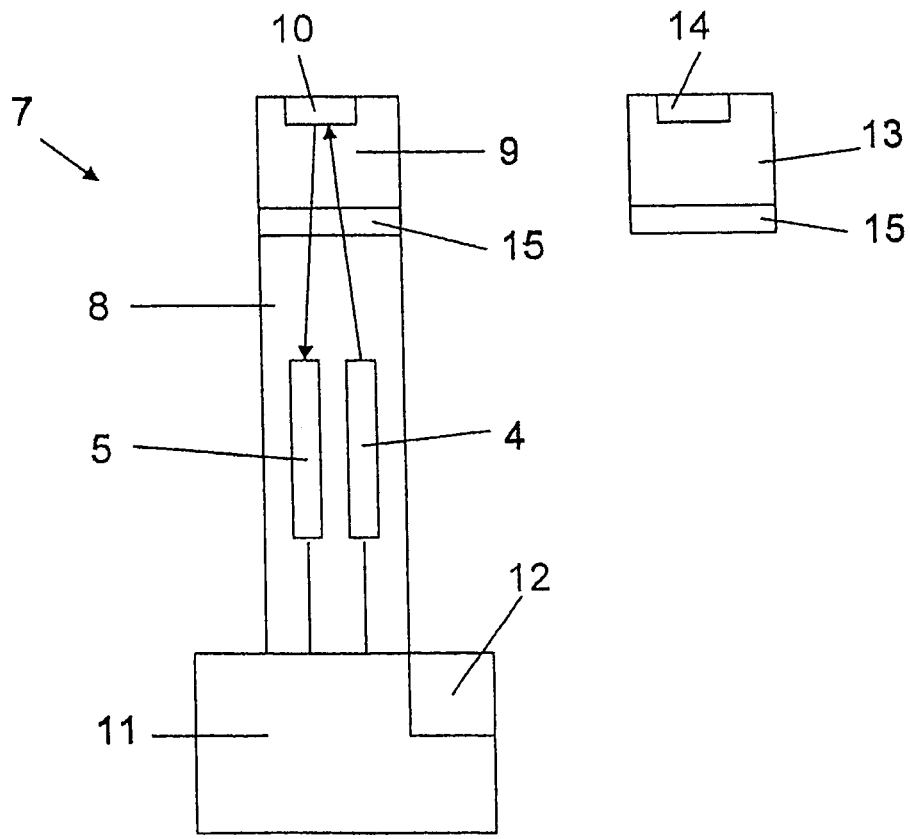
FIG. 2 is a form of embodiment for an optical sensor of the invention.

An example of the proposed optical sensor 7 according to the invention is presented in FIG. 2. Optical sensor 7 comprises a housing 8 and a cap 9. The fluorescing layer 10 is arranged internally in the cap. In the present example fluorescing layer 10 is able to determine the pH value of the medium to be examined. Cap 9 is connected to housing 8 via a plug, or rotary, closure, which is embodied as standard interface 15.

Optical transmitter 4 and at least one optical receiver 5 are arranged in housing 8 on the end facing cap 9. Optical transmitter 4 and optical receiver 5 are electrically connected to a sensor electronics 11 likewise located in housing 8, wherein sensor electronics 11 has a memory 12. Light characteristics of various fluorescing layers 10 are stored in memory 12. Thus, for example, light characteristics of fluorescing layers 10 are stored, which determine, in addition to pH value, oxygen or hydrogen or chlorine in the medium to be examined. Among these light characteristics are the most varied of light intensities, the light frequencies or wavelengths and different decay curves. These light characteristics stored in the memory serve as reference patterns.

As already explained, cap 9 is connected with housing 8 via standard interface 15 in the form of a plug or rotary connection. In this way, cap 9 can be simply removed from housing 8 and replaced by another cap 13, which, for example, is suitable for the concentration measurement of oxygen.

After the manufacture of housing 8, which contains optical transmitter 4, optical receiver 5 and sensor electronics 11, cap 9, 13 is set on housing 8 at the end of production. Cap 9, 13 has a desired fluorescing layer 10, 14, which, for example, permits the determining of the oxygen concentration in the medium to be examined. Thus simply an oxygen sensor is produced.

If cap 13 having fluorescing layer 14 is mechanically secured on housing 8, there is triggered in sensor electronics 11 a calibration procedure, which starts a recognition method. In this recognition method, sensor electronics 11 is activated to output a signal to optical transmitter 4, which thereon transmits a light beam, which is radiated back from the fluorescing layer 14. Receiver 5 converts the light radiated back from fluorescing layer 14 to an electrical signal, which, in turn, is fed to sensor electronics 11. Sensor electronics then compares the received light characteristic to reference patterns stored in memory 12 for different fluorescing layers 10, 14. In this way, sensor electronics 11 recognizes that fluorescing layer 14 for determining the concentration of oxygen is located in the attached cap 13. On the basis of this information, sensor electronics 11 calls for the following concentration measurement the likewise stored, corresponding evaluating method for oxygen. This calibration procedure is repeated after each replacement of the cap, and consequently, replacement of the fluorescing layer.

By means of this embodiment only a single sensor electronics is required for the evaluation of different fluorescing layers 10, 14. Thus, the sensor electronics 11 can process the most varied of measurement parameters with a corresponding availability of the evaluating methods needed for different materials. By changing caps 9, 13 containing different sensitive elements, not only is the measurement parameter changed, but different measuring ranges can also be selected. New measurement parameters can be added simply by updating the firmware within sensor electronics 11, so that in embarking upon the production of a new sensor only the software within sensor electronics 11 must be changed.

Instead of standardizing the sensor components, only housing 8 is manufactured, which, in addition to optical transmitter 4 and optical receiver 5, contains sensor electronics 11. This optical sensor 7 has not only advantages in manufacturing, where only different sensor heads in the form of caps 9, 13 having different sensitive elements 10, 14 must be provided, but it can also be advantageous for customers, who must only have one housing 8 with sensor electronics 11, in order to ascertain different measurement parameters. To this end, the customer just places cap 9, 13 having the desired fluorescing layer 10, 14 on housing 8 and thereupon obtains a new optical sensor for the measurement of another measurement parameter.

The invention claimed is:

1. A method for determining substance concentrations in aqueous solutions by means of a fluorescence measurement with an optical sensor, the sensor comprising:
   a housing;
   sensor electronics;
   an optical transmitter;
   an optical receiver; and
   a sensor head, which contains a sensitive element and which is adjoined by said housing, said housing containing said sensor electronics; and
   wherein said sensor head and said housing are separable, wherein different sensor heads having different sensitive elements are connectable to said housing containing said sensor electronics;
   the method comprising the steps of:
   irradiating said sensitive element with light from said optical transmitter, wherein said sensor electronics excites said optical transmitter;
   radiating back a light characteristic by said sensitive element;
   detecting said back-radiated light characteristic by said optical receiver;
   forwarding said back-radiated light characteristic from said optical receiver to said sensor electronics;
   evaluating said back-radiated light characteristic by said sensor electronics, wherein said light characteristics are generated by said different sensitive elements; and
   recognizing said sensitive element in said sensor head automatically by said sensor electronics by comparing said back-radiated light characteristic with stored measurement data and/or characteristic lines for recognizing said sensitive element.

2. The method as claimed in claim 1, wherein:
   the stored measurement data comprise light intensities and/or light frequencies and the characteristic lines comprise the decay curves of the light intensity of the back-radiated light characteristic.

3. The method as claimed in claim 1, wherein:
   said sensor electronics has an electrical current source.

4. The method as claimed in claim 1, wherein:
   said sensor head and said housing are optically and mechanically connected to one another via a standard interface.

5. The method as claimed in claim 1, wherein:
   said sensor head is cap-like.

6. The method as claimed in claim 5, wherein:
   said cap-like sensor head or said housing has a sealing element, which seals off said standard interface from the environment.

7. The method as claimed in claim 1, wherein:
   said sensitive element is a sensitive layer.

8. The method as claimed in claim 1, wherein:
   said housing contains an optical transmitter and an optical receiver, which are connected to said sensor electronics; and
   said sensor electronics has a memory containing said measurement data and/or characteristic lines of the light characteristics of the different sensitive elements.

9. The method as claimed in claim 2, wherein:
   said light characteristics stored in the memory serve as reference patterns.

10. The method as claimed in claim 1, further comprising the step:
    calibrating or initializing by activating the optical transmitter by said sensor electronics, wherein said optical transmitter radiates light on the sensitive element.

11. The method as claimed in claim 1, further comprising the step:
    feeding the back-radiated light characteristic to the sensor electronics, which automatically detects the measurement parameter to be determined, and
    selecting by said sensor electronics an evaluating method which corresponds to a determined measurement parameter and with which following concentration measurement methods are executed.

12. The method as claimed in claim 7, wherein:
    said sensitive layer detects oxygen, hydrogen, chlorine, or pH value.

* * * * *